United States Patent

Onan et al.

[11] Patent Number: 5,869,750
[45] Date of Patent: Feb. 9, 1999

[54] METHOD, SYSTEM AND DEVICE FOR TESTING TWO-PHASE COMPRESSIBLE COMPOSITIONS HAVING GAS UNDER PRESSURE

[75] Inventors: David D. Onan; Billy J. Bennett; John L. Brumley; Norman A. Sayers, all of Duncan, Okla.

[73] Assignee: Halliburton Energy Services, Inc., Duncan, Okla.

[21] Appl. No.: 947,410

[22] Filed: Oct. 8, 1997

[51] Int. Cl.$^6$ .................................................. G01N 33/00
[52] U.S. Cl. ......................................................... 73/64.41
[58] Field of Search ........................... 73/64.41, 38, 794, 73/152.18, 152.27, 152.55; 166/293, 285, 309

[56] References Cited

U.S. PATENT DOCUMENTS

| | | | |
|---|---|---|---|
| 3,286,510 | 11/1966 | Parker | 73/53 |
| 4,259,868 | 4/1981 | Rao et al. | 73/597 |
| 4,380,266 | 4/1983 | Wellington | 166/252 |
| 4,409,662 | 10/1983 | Rao | 364/557 |
| 4,430,889 | 2/1984 | Sutton | 73/61.4 |
| 4,567,765 | 2/1986 | Rao et al. | 73/597 |
| 4,648,264 | 3/1987 | Freese et al. | 73/64.1 |
| 4,691,558 | 9/1987 | Vinson et al. | 73/64.1 |
| 4,700,567 | 10/1987 | Frey et al. | 73/152.01 |
| 4,823,594 | 4/1989 | Gray | 73/54.01 |
| 5,325,723 | 7/1994 | Meadows et al. | 73/794 |
| 5,329,811 | 7/1994 | Schultz et al. | 73/152.02 |

Primary Examiner—Hezron Williams
Assistant Examiner—Jay L. Politzer
Attorney, Agent, or Firm—Craig W. Roddy; E. Harrison Gibert, III

[57] ABSTRACT

A method and system for testing a two-phase compressible composition, such as a foamed cementing composition, enables testing for mechanical properties while maintaining original pressurized gas volumes in the composition. A specimen of the composition can be prepared, transferred and tested without disrupting the dynamic status of the specimen. This allows for testing of the composition under conditions in which the composition will be placed in an oil or gas well. A related specimen test device is also disclosed. The method includes pressurizing the two-phase compressible composition in a first vessel to a pressure greater than atmospheric pressure; pressurizing a second vessel to the pressure; transferring at least a portion of the composition from the first vessel to the second vessel while maintaining at least substantially the pressure on the transferred portion of the composition; and testing the portion of the composition transferred to the second vessel, which testing is performed while maintaining at least substantially the pressure in the second vessel.

23 Claims, 4 Drawing Sheets

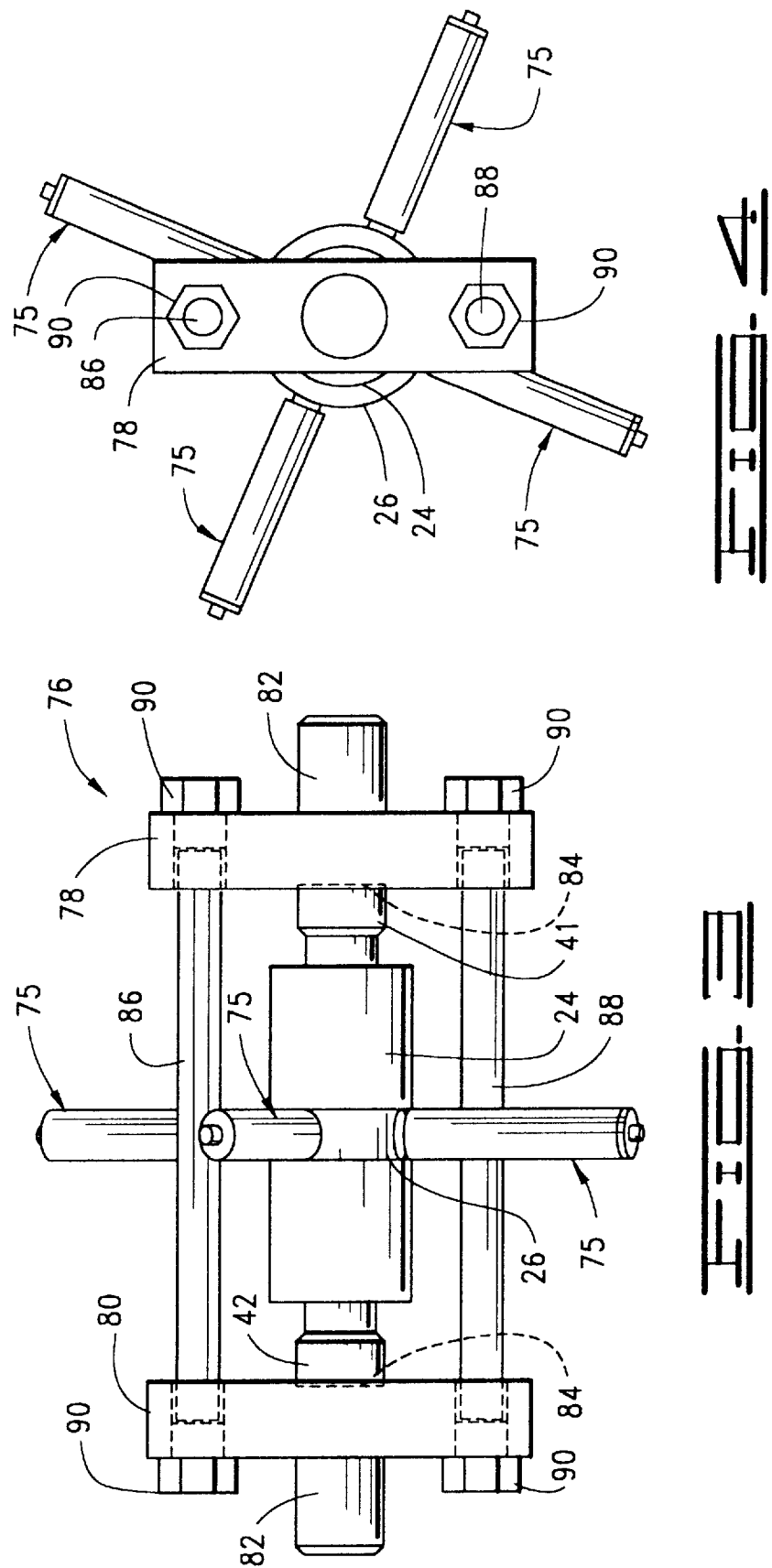

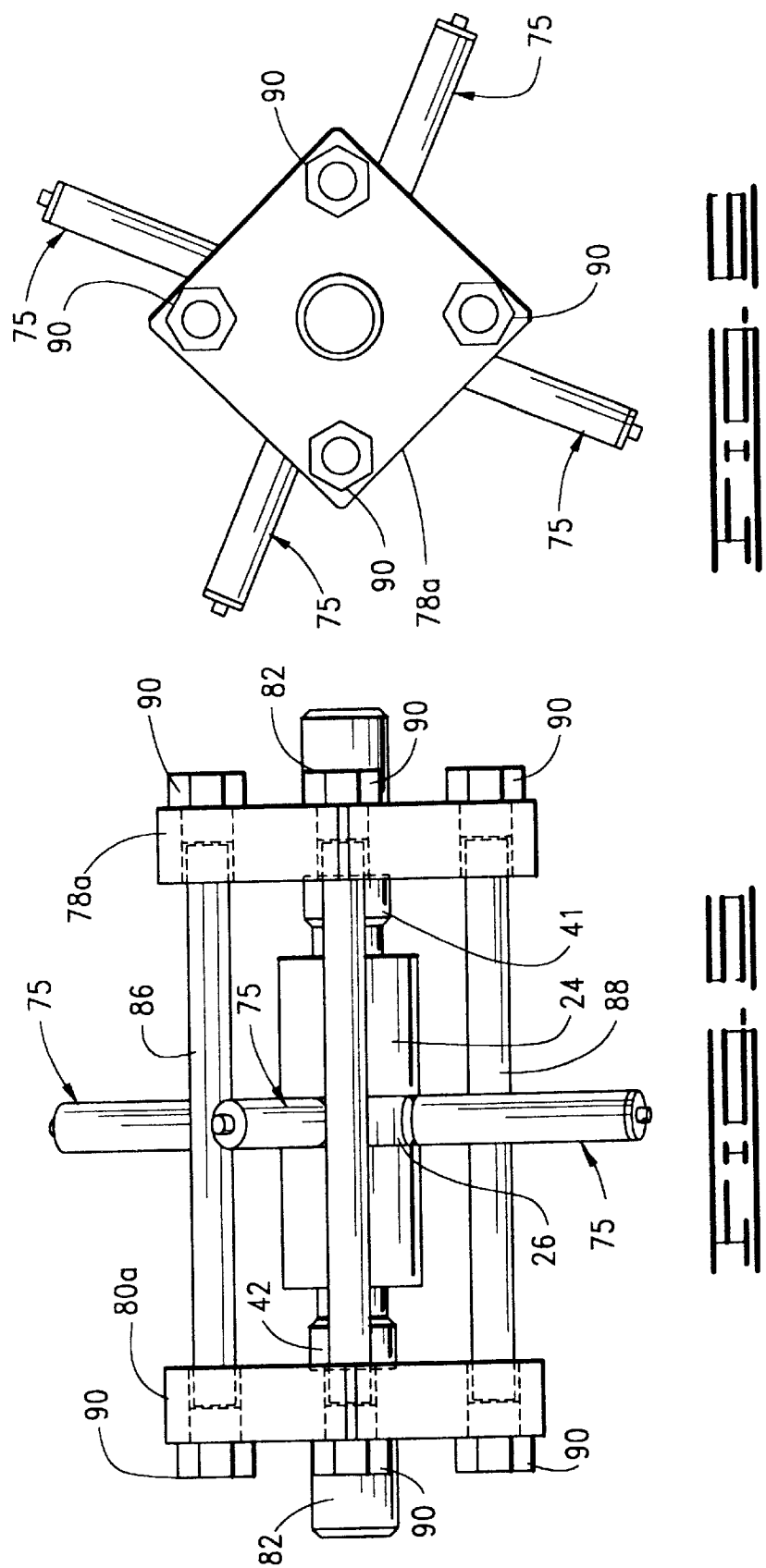

5,869,750

METHOD, SYSTEM AND DEVICE FOR TESTING TWO-PHASE COMPRESSIBLE COMPOSITIONS HAVING GAS UNDER PRESSURE

BACKGROUND OF THE INVENTION

This invention relates generally to methods for testing two-phase compressible compositions having gas under pressure. Examples of these compositions are foamed cementing compositions used in the oil and gas industry. This invention also relates to systems and devices which can be used in such methods.

A growing trend in the oil and gas industry is the use of foamed cementing compositions, which are made by foaming a Portland-based cementing composition with a gas (preferably an inert gas), a foamer and a foam stabilizing agent. Such compositions have mechanical property advantages and operability advantages over conventional, non-foamed Portland-based cementing compositions. For example, conventional compositions undergo shear failure whereas foamed cementing compositions undergo plastic failure under stress/stress cycle loading. Susceptibility to plastic failure as opposed to shear failure is preferred because of the prolonged well life expected or provided as a result of increased resiliency/stress resistance. Shear failure of an annular cement sheath generally results in loss of zonal isolation, annular pressure build-up, collapsed casing, etc.

With all types of cementing compositions, the ability to test them is desired. For example, a conventional composition can be tested in any of various types of equipment. Two particular test units are the MACS Analyzer and the triaxial load cell, both from Halliburton Energy Services. If both of these devices are used to test a conventional cementing composition, a sample of the composition is put into or made in a pressurizable chamber of the MACS Analyzer and tested there for properties such as compressibility, thickening time, and static gel strength. A portion of this sample or another sample of the composition can be allowed to harden into a core and separately put in the triaxial load cell for testing of mechanical properties such as Young's modulus and Poisson's ratio. It would be desirable to perform the same tests on foamed cementing compositions so that the same test data can be developed for this class of material. These tests can be performed as described above; however, there has been a shortcoming which can adversely affect the significance of such testing as applied to foamed cementing compositions, or other two-phase compressible compositions having entrained gas under pressure.

The entrained gas contained in the pore spaces within the matrix of the composition is allowed to escape to the atmosphere as a function of the specimen's permeability if it is not kept under suitable pressure. The shortcoming of prior test methods and systems is that they have not enabled a specimen to be made under pressure, such as in the MACS Analyzer, transferred under pressure to another test device, such as the triaxial load cell, and then tested under pressure whereby the two-phase integrity of the specimen is maintained throughout the entire process. Because the actual composition used in an oil or gas well will remain under pressure in the wellbore, such prior techniques which allow for the gaseous phase to escape before testing may not produce meaningful test data relative to the actual composition that will exist in the well. Accordingly, there is the need for a method and system for testing such a composition while maintaining the integrity of the test specimen.

SUMMARY OF THE INVENTION

The present invention overcomes the above-noted and other shortcomings of the prior art and satisfies the aforementioned need by providing a novel and improved method and system for testing a two-phase compressible composition, such as a foamed cementing composition. The invention provides for testing for mechanical properties while maintaining original pressurized gas volumes. A specimen of the composition can be prepared, transferred and tested without handling or disrupting the dynamic status of the specimen. This allows for testing of the composition under pressure and temperature conditions simulating those in an oil or gas well.

The method of the present invention for testing a two-phase compressible composition comprises pressurizing the two-phase compressible composition in a first vessel to a pressure greater than atmospheric pressure and pressurizing a second vessel to the pressure. The method further comprises transferring at least a portion of the composition from the first vessel to the second vessel while maintaining at least substantially the pressure on the transferred portion of the composition. The method still further comprises testing the portion of the composition transferred to the second vessel, which testing is performed while maintaining at least substantially the pressure in the second vessel. The method can additionally comprise determining when a sufficient amount of the composition has been transferred into the second vessel; this includes sensing a lateral dimension of the portion of the composition retained in the second vessel.

A more specific definition of the present invention is as a method of testing a foamed cementing composition. This comprises preparing a foamed cementing composition in a vessel having a paddle. This includes creating relative rotation between the paddle and the vessel and flowing a gas into the vessel under a pressure greater than atmospheric pressure. The method further comprises increasing the pressure in the vessel to a test pressure simulating a pressure in an oil or gas well, pressurizing a hydraulic fluid chamber to the test pressure, and pressurizing a transfer flow collection chamber to the test pressure. The method still further comprises communicating the pressurized hydraulic fluid chamber with the exterior of a sleeve retained in a specimen test device and communicating the pressurized transfer flow collection chamber with the interior of the sleeve in the specimen test device. The method additionally comprises: communicating the pressurized vessel with the interior of the sleeve in the specimen test device, and relieving the pressure in the transfer flow collection chamber to allow flow from the pressurized vessel to the pressurized transfer flow collection chamber such that a portion of the foamed cementing composition is transferred into the sleeve of the specimen test device without disrupting the pressurized state of the foamed cementing composition. This method can further comprise: determining when a sufficient amount of the foamed cementing composition is transferred into the sleeve in the specimen test device; disconnecting the specimen test device from the vessel, the hydraulic fluid chamber and the transfer flow collection chamber while maintaining pressure in the specimen test device such that the pressurized state of the portion of the foamed cementing composition in the specimen test device is not disrupted; and testing the portion of the foamed cementing composition in the sleeve of the specimen test device under the maintained pressure.

The system of the present invention is for preparing, transferring and testing a foamed cementing composition.

This system comprises: a vessel to receive constituents for creating a foamed cementing composition under pressure; a source of a fluid for foaming the cementing composition; a pressure booster having an inlet connected to the source of a fluid and having an outlet connected to the vessel; a specimen test device having a sleeve disposed therein; a hydraulic fluid chamber; a transfer flow collection chamber; a first valve, which first valve is connected to an outlet of the vessel and to an inlet of the specimen test device; a second valve, which second valve is connected to the hydraulic fluid chamber and to the specimen test device such that the second valve controls communication of pressure from the hydraulic fluid chamber with an exterior of the sleeve; a third valve, which third valve is connected to the transfer flow collection chamber and to the specimen test device such that the third valve controls communication of pressure from the transfer flow collection chamber with an interior of the sleeve; means for connecting the pressure booster with the hydraulic fluid chamber; and means for connecting the pressure booster with the transfer flow collection chamber.

The present invention also provides a specimen test device that comprises: a triaxial load cell; and a support structure mounted on the triaxial load cell, which support structure includes: a first end plate which is disposed adjacent one end of the triaxial load cell, a second end plate which is disposed adjacent another end of the triaxial load cell, and a plurality of connecting members slidably received by the first and second end plates, which connecting members define a maximum spacing between the first and second end plates but permit the first and second end plates to move relatively towards each other along the connecting members.

Therefore, from the foregoing, it is a general object of the present invention to provide a novel and improved method, system and device for testing two-phase compositions having gas under pressure. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 3 is a side view of one preferred embodiment of the specimen test device of the present invention.

FIG. 4 is an end view of the specimen test device shown in FIG. 3.

FIG. 5 is a side view of another preferred embodiment of the specimen test device of the present invention.

FIG. 6 is an end view of the specimen test device shown in FIG. 5.

DETAILED DESCRIPTION OF THE INVENTION

A preferred embodiment of the system of the present invention will be described with reference to FIGS. 1 and 2. This system is one especially for preparing, transferring and testing a foamed cementing composition; however, the present invention can be generally applied to other two-phase compressible compositions having gas entrained at a pressure greater than atmospheric pressure.

Figure 1:
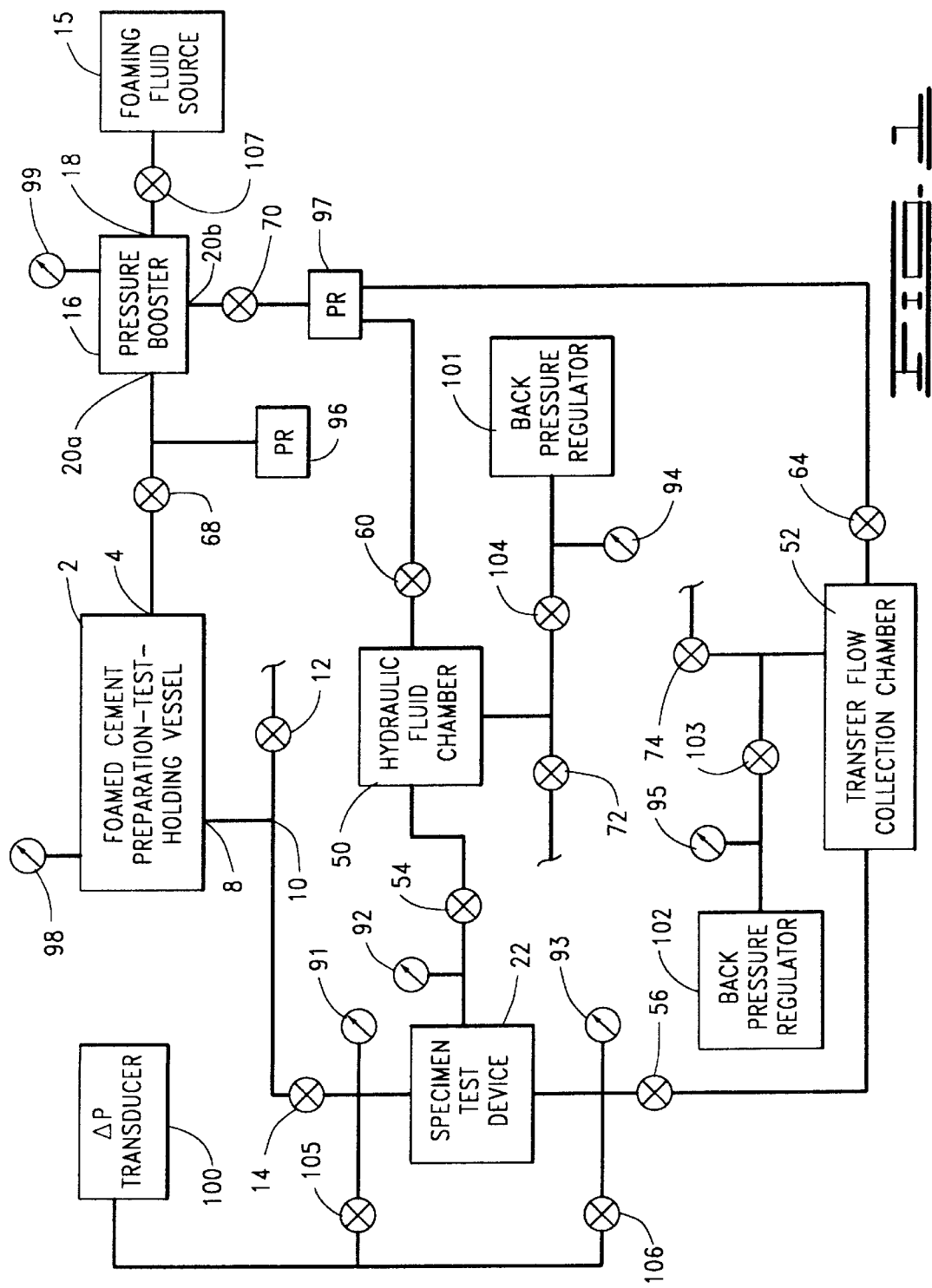
FIG. 1 is a schematic block diagram of the preferred embodiment system of the present invention.

The system shown in FIG. 1 includes a vessel 2 to receive constituents for creating the foamed cementing composition under pressure. A particular implementation for the vessel 2 is in the MACS Analyzer from Halliburton Energy Services of Duncan, Okla. The MACS Analyzer is the subject of U.S. Pat. No. 4,648,264 to Freese et al., which is incorporated herein by reference. The MACS Analyzer includes a high pressure, high temperature container implementing the vessel 2. This is disposed within a metallic shield. A jacket of suitable insulating material is disposed around the outside of the container. Cooling water lines communicate with the interior of the container. The interior of this implementation of the vessel 2 defines a chamber into which the sample of a fluid to be tested is received. The inner surface defining this chamber is coated with a nickel-based alloy to resist corrosion which might occur from the fluids when they are pressurized up to the high pressures that can be applied by the present invention. The contents of this chamber can be pressurized through a pressurizing fluid inlet port defined through a cap member releasably secured to the container by means of a retaining ring. The pressurizing fluid inlet is identified in the schematic of FIG. 1 by the reference numeral 4. In addition to being pressurized, the container and the sample contained in the chamber thereof can be heated by suitable heating bands which are electrically energized.

Figure 2:
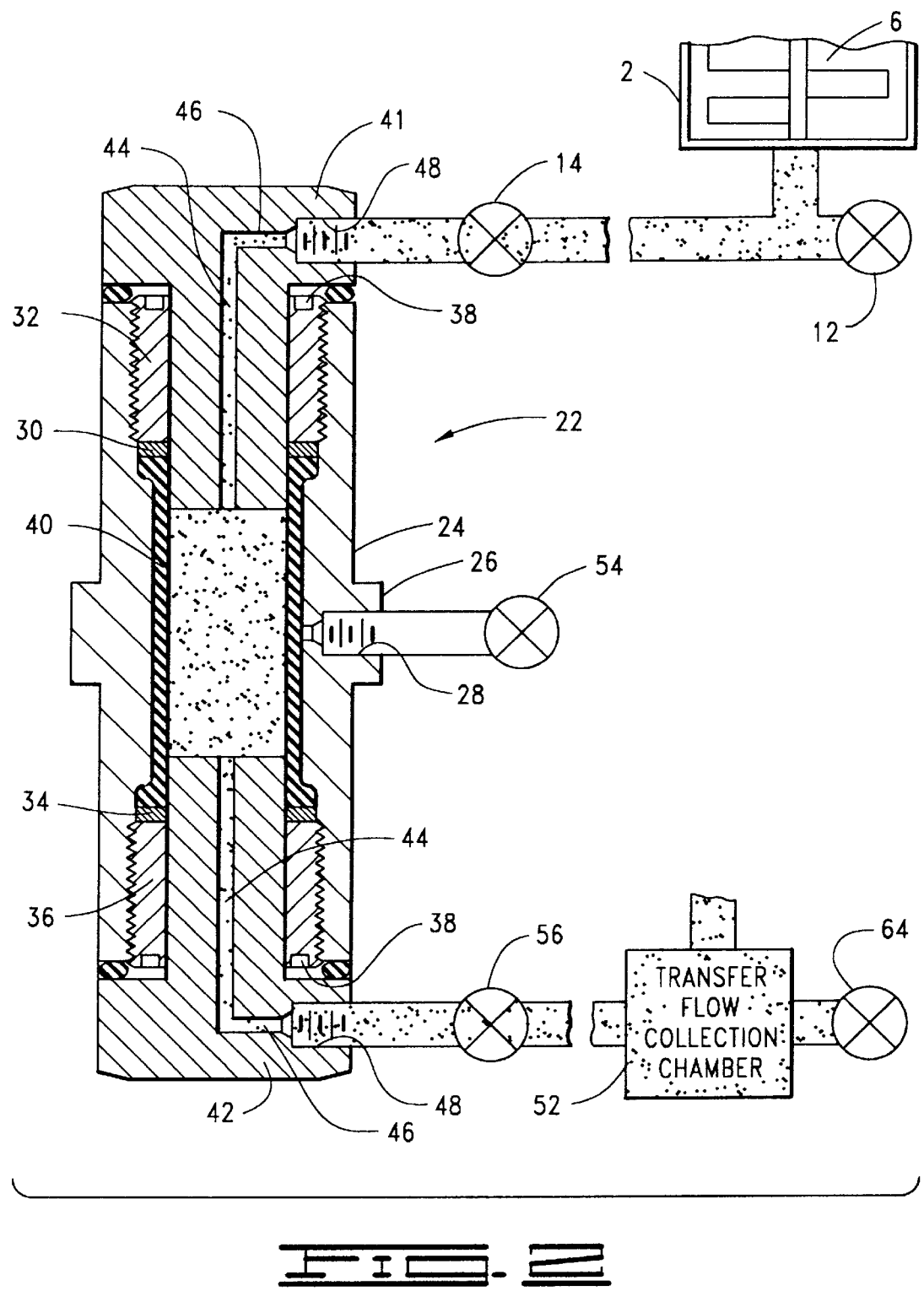
FIG. 2 illustrates a particular implementation of part of the system shown in FIG. 1, and it also shows placement of a composition at a particular stage in the method of the present invention.

Forming another part of the vessel equipment of the preferred embodiment is a paddle 6 schematically illustrated in FIG. 2. The paddle has a support shaft from which paddle wings extend. The support shaft is associated with a drive shaft forming part of a magnetic drive mechanism. The paddle can be constructed as a single unit or as a split paddle wherein one portion of the paddle rotates one revolution before engaging the other portion for thereafter driving the second portion as the first portion is further rotated. Located at the top of the paddle is a slurry isolation plate having a plurality of holes for permitting communication between the slurry contained above and below the plate. The plate allows a layer of static slurry to form as an isolating barrier between the slurry engaged by the paddle and the pressurizing fluid maintained above the isolation plate. A biasing spring extends between the isolation plate and seal and support members.

To withstand the high pressures which can be applied within the chamber of the vessel 2, the container and the cap member of the vessel are constructed of heavy, durable material. To facilitate raising and lowering the heavy cap member relative to the container, a fluid-actuated hoist means is included as another portion of the test chamber equipment of the MACS Analyzer.

The pressurizing circuit of the MACS Analyzer applies a pressure to the sample within the chamber of the vessel 2. This pressure is established through a pressurizing fluid flowed into the chamber through the inlet port 4. In the preferred embodiment, the pressurizing fluid is nitrogen; however, other types of fluids can be used. The pressure within the vessel 2 can be monitored through a gauge (illustrated as gauge 98 in FIG. 1) forming part of the MACS Analyzer.

The vessel 2 includes an outlet port 8 through which the composition in the vessel can be released and through which the vessel can be flushed for cleaning.

A conventional MACS Analyzer can be modified and prepared for a foamed cement composition in the following manner, for example. The vessel 2 is cleaned as are the paddle assembly and the isolation cavity in the lid. The drain hole 8 in the bottom of the test chamber is also cleaned. The paddle assembly is assembled by first placing a small metal washer on the shaft, then a flat rubber diaphragm, a metal diaphragm support with a small spring positioning washer on the bottom, and a ⅜ inch inner diameter by ½ inch outer diameter TEFLON O-ring on the shaft. The TEFLON O-ring is pushed upward onto the shaft so the diaphragm and the washers contact the inside of the lid. They are used to prevent foamed cementing composition from entering the magnetic drive equipment. A one-piece paddle is placed on the shaft and retained with a shear pin, washer and screw. When preparing a slurry for transfer, it is preferred that the one-piece paddle be used in an attempt to obtain better balance of the paddle when it is rotating at high speed during foaming of the slurry. If a static gel strength test is to be performed, the two-piece paddle is preferably used (the MACS Analyzer can be used for conducting static gel strength, compressive and thickening time tests on the composition). The standard dump lines from below the vessel 2 are removed and replaced with a T-connection 10 having one branch connected to a valve 12 and the other branch connected to a valve 14 through suitable conduits as needed.

With the standard isolation plate used above the paddle in the MACS Analyzer, the foamed cementing composition may migrate above it into the lid cavity when preparing and performing tests on these compositions. This can allow the cement to also migrate up into the magnetic drive area and cause excess friction and the need to disassemble and clean the drive more often. Due to the absence of stirring above the standard isolation plate, there may be density variations within the slurry below and above the isolation plate. With the standard isolation plate, it is sometimes more difficult to define the volume the foamed cement composition will occupy inside the chamber when preparing the foam. The use of a special isolation plate above the paddle in the MACS Analyzer when testing foam cement slurries normally will result in better containment of the slurry within the stirring portion of the test chamber. Such a special isolation plate is available from Halliburton Energy Services; it includes a center plate having holes which allow the pressurizing fluid to enter the vessel chamber by opening a spring loaded bottom plate, then the spring loaded diaphragm normally prevents the slurry from coming back into the cavity above the isolation plate. The special isolation plate can be made from any suitable material (e.g., stainless steel, brass or steel). Stainless steel or brass are normally preferred since they will not rust or corrode. The use of aluminum is not recommended since the slurry can react with the aluminum causing a gas to be generated which can affect the test results.

The following instructions are for making, assembling and installing the special isolation plate:

1. The bottom plate contains a 0.5 inch hole in the center for the paddle shaft to go through and three 0.1875 inch holes around the side for connecting rods.
2. The bottom end of the connecting rods are to be welded (or brazed, silver soldered, etc.) to the top side of the bottom plate. They should be vertical to the plate so the center and top plates will fit over the rods.
3. Place a rubber disc onto the connecting rods above the bottom plate. The top of the rubber disc should be coated with a thin coating of grease to help seal against the isolation plate. The rubber disc can be made from a Halliburton Energy Services part number 800.62183 diaphragm, which is used in the high-pressure, high-temperature consistometer slurry cup, by enlarging the center hole to 0.375 inches. Enlarging the hole can be accomplished either by cutting it (e.g., with a stopper hole cutter) or by running a round file through it several times. To enlarge the hole with a round file, start with a file slightly larger than the original hole in the center of the diaphragm and increase to larger sizes until the diaphragm fits on the MACS Analyzer's paddle shaft with only a slight drag.
4. Place a modified Halliburton Energy Services part number 800.59549 center isolation plate which has had the outside diameter turned to 3.96 inches (with the outer holes which are on a 3 inch diameter brazed shut) on top of the rubber diaphragm. This plate has several small holes (approximately 0.125 inches in diameter —the size and location of these holes is not important) and inside the center 2.75 inch (or smaller) diameter area on the plate to allow the nitrogen to enter the test chamber.
5. Place a Halliburton Energy Services part number 800.59554 spring on top of the center plate.
6. Place the top plate over the spring, compress the spring enough that its top will be below the holes in the top of the connector rods. While compressing the spring, install the retaining pins (e.g., such as pieces of a small paper clip) into the holes in the connector rods and bend them so they will not come out.
7. With the paddle removed from the MACS Analyzer's paddle shaft, install the special isolation plate onto the shaft with the diaphragm portion at the bottom, install the top paddle section, install the paddle holding pin (if the SGS split paddle is used, install the Halliburton Energy Services part number 70.33411 TEFLON O-ring, the bottom paddle blade and the Halliburton Energy Services part number 800.59623 washer) and then the Halliburton Energy Services part number 70.45608 screw into the bottom of the paddle shaft. Coat the outside diameter of the isolation plate with a thin coating of grease to help seal the plate against the inside of the chamber before placing the lid assembly into the chamber.

The system shown in FIG. 1 further includes a source of a fluid for foaming the cementing composition. This can be, for example, commercially available bottled nitrogen pressurized up to about 1,500 lbs. per square inch (psi). Other foaming fluid sources can be used, such as compressed air, carbon dioxide, etc. The foaming fluid source is identified in FIG. 1 by the reference numeral 15.

The system depicted in FIG. 1 also includes a pressure booster 16 having an inlet 18 connected through a valve 107, such as a commercially available high pressure needle valve, to the foaming fluid source 15. The pressure booster 16 also has an outlet 20a connected to the foamed cement preparation-test-holding vessel 2 through a valve 68, such as a commercially available high pressure needle valve. In a particular implementation, the pressure booster 16 is an in-line gas intensifier, such as a 25:1 compression ratio single action pneumatic gas booster compressor. The gas intensifier increases the nitrogen pressure above that available from the foaming fluid source 15 alone. Preferably this pressure simulates the pressure in an oil or gas well, such as a pressure up to 11,000 psi.

The system shown in FIG. 1 also includes a specimen test device 22. This is preferably implemented with a triaxial load cell such as of the type provided by Halliburton Energy Services. One type is disclosed in U.S. Pat. No. 5,325,723 to Meadows et al. and another is disclosed in pending U.S.

Patent Application filed Jul. 1, 1997, Ser. No. 08/886,789 (HES 96.0093 U1), entitled "Core Sample Test Method and Apparatus" assigned to the assignee of the present invention, both of which are incorporated herein by reference. An example of such a triaxial load cell is illustrated in FIG. 2.

Referring to FIG. 2, the Halliburton triaxial load cell comprises a body or housing 24. A circumferential flange 26 protrudes radially outwardly from the central portion of the support body 24. Four diametrically opposed openings are defined radially through the flange 26 for a purpose to be described subsequently with regard to FIGS. 3–6. An opening 28 angularly offset from these other four openings is also defined through the flange 26 as shown in FIG. 2.

Removable parts of the triaxial load cell 22 include: an annular washer 30; an exteriorly threaded annular holding member 32 connected to the interior of the support body 24 and adjacent the washer 30 to hold it in place; an annular washer 34; and an exteriorly threaded annular holding member 36 connected to the interior surface of the support body 24 and adjacent the washer 34 to hold it in place. The holding members 32, 36 have sockets 38 defined in their outer ends for receiving a spanner wrench to screw and unscrew the members 32, 36 relative to the support body 24.

The triaxial load cell further comprises a sealing sleeve 40. This is supported inside the housing 24 and adapted to receive the sample of the foamed cementing composition to be tested. The sleeve 40 is made of a resilient material of a type known in the art, and is preferably what is referred to as a Hassler sleeve.

The triaxial load cell also comprises retaining means for releasably retaining the hardened sample within the sealing sleeve 40 and for transferring a longitudinal force to the hardened sample. The retaining means of the preferred embodiment illustrated in FIG. 2 includes two end caps 41, 42 slidably received in the housing 24 (specifically, within the washer/holding member pairs 30, 32 and 34, 36, respectively). Each end cap 41, 42 has an axial channel 44 and an intersecting radial channel 46. Each channel 44 opens through the end of the respective end cap that is adjacent a respective end of the sample when the sample is within the sleeve 40. Each channel 46 opens through the side of its respective end cap via a respective port 48. Each of the end caps 41, 42 has a smaller diameter cylindrical portion that is received into the housing 24 and a larger diameter cylindrical portion that is outside the housing 24 as shown in FIG. 2. The sides of the smaller diameter portions are preferably smooth so that the end caps can be easily pushed in and pulled from the housing 24 when there is no test pressure being applied.

Heater bands (not shown) may be mounted adjacent the outer surface of the support body 24 in a convention manner to provide heat for controlling the temperature under which the sample in the sleeve 40 is tested.

The system shown in FIG. 1 also includes a hydraulic fluid chamber 50. In a particular implementation, the hydraulic fluid chamber 50 is a commercially available multiported constant volume chamber rated for the operating pressure of the system. Associated with the chamber 50 is a conventional back pressure regulator circuit having a back pressure regulator 101 connected with a needle valve 104 and a pressure gauge 94.

The system shown in FIG. 1 also includes a transfer flow collection chamber 52, such as implemented by a heavy gauged steel wall vessel. Associated with the chamber 52 is a conventional back pressure regulator circuit having a back pressure regulator 102 connected with a needle valve 103 and a pressure gauge 95.

The aforementioned components of the system shown in FIG. 1 are connected by suitable flow lines and valves as shown in the drawing. These include the valves 12 and 14 already referred to. The valve 14 is connected to the outlet 8 of the vessel 2 and to the inlet port 48 of the end cap 41 of the triaxial load cell implementing the specimen test device 22 illustrated in FIG. 2.

A valve 54 is connected to the hydraulic fluid chamber 50 and to the inlet port 28 of the triaxial load cell implementing the specimen test device 22 illustrated in FIG. 2. The valve 54 controls communication of pressure from the hydraulic fluid chamber 50 with an exterior of the sleeve 40. A specific implementation of the valve 54 is a commercially available high pressure needle valve.

A valve 56 is connected to the transfer flow collection chamber 52 and to the port 48 of the end cap 42 of the triaxial load cell implementation of the specimen test device 22. The valve 56 controls communication of pressure from the transfer flow collection chamber 52 with the interior of the sleeve 40. A specific implementation of the valve 56 is a commercially available full opening ball valve which allows cleaning of solid material from the flow lines.

The system shown in FIG. 1 further includes means for connecting the pressure booster 16 with the hydraulic fluid chamber 50. Although any suitable means for connecting can be used, the illustrated implementation includes (1) a valve 70 connected to output 20b of the pressure booster 16, (2) a valve 60 connected to a port of the hydraulic fluid chamber 50, and (3) a pressure regulator 97 connected to valves 60 and 70. Valves 60 and 70 can be implemented by commercially available high pressure needle valves the same as valve 54. The pressure regulator 97 can be implemented by a commercially available device suitable for the control of gas supply pressure.

The system of FIG. 1 also includes means for connecting the pressure booster 16 with the transfer flow collection chamber 52. This includes the valve 70, the pressure regulator 97 and a valve 64, such as a commercially available high pressure needle valve, connected to a port of the transfer flow collection chamber 52.

Also included in the system shown in FIG. 1 is a valve 72 connected to a port of the hydraulic fluid chamber 50. A valve 74 is connected to a port of the transfer flow collection chamber 52. In a particular implementation the valves 72, 74 are precision needle valves for flow shut off and control.

The foregoing components of the system are constructed of suitable materials to withstand the pressures and temperatures that can be applied for obtaining the desired tests at known wellbore conditions. The system also includes any suitable and necessary pressure relief safety devices, such as rupture disks. The specimen test device 22 of a particular implementation of the present invention also includes a support structure mounted on the triaxial load cell. This is illustrated in two embodiments, one of which is shown in FIGS. 3 and 4 and the other of which is shown in FIGS. 5 and 6.

Referring to FIGS. 3 and 4, the triaxial load cell is generally identified by the reference numerals 24, 41 and 42, respectively designating the body and two ends caps of the embodiment shown in FIG. 2. FIGS. 3 and 4 also show four lateral deflection sensors 75 mounted in the four openings defined through the flange 26 of the body 24 of the triaxial load cell. The lateral deflection sensors 75 sense changes in the lateral dimensions of the sample specimen contained within the sleeve 40. The sensors have respective probes communicating through the sealing sleeve 40 to detect lateral changes in the sample. Each of the sensors includes a direct current linearly variable differential transducer assembly of a type used in prior triaxial load cells. Although not shown in the figures, longitudinal deflection sensors can also be used in known manner. These are attached by suitable support brackets (not shown) attached to the end caps 41, 42. These measure longitudinal displacement of the sample in the sleeve 40. These are direct current linearly variable differential transducers of the same type as can be used for the lateral deflection sensors.

To enable the triaxial load cell to withstand the pressures applied using the system of FIG. 1, a support structure 76 is used. The support structure 76 includes end plates 78, 80. Specific implementations of the end plates 78, 80 include solid metal stock with integral knobs or pedestals protruding axially therefrom. These are identified in FIG. 3 by the reference numeral 82. Each end plate 78, 80 also includes an axial cavity 84 for receiving the end of a respective one of the end caps 41, 42.

Each of the end plates 78, 80 also includes two apertures near outer edges. These apertures receive respective connecting members 86, 88. The diameters of the members 86, 88 are slightly smaller than the diameters of the apertures in the end plates so that the end plates can slidably move along the members 86, 88. The members 86, 88 are implemented as bolts with threaded ends that receive respective nuts 90. The nuts 90 threaded on the bolts 86, 88 limit the maximum spacing between the two end plates 78, 80.

The ability to move along the members 86, 88 between the nuts 90 is needed so that the triaxial load cell can be loaded by a conventional loading machine pressing against the outer ends of the knobs or pedestals 82 extending outwardly from each of the end plates 78, 80. Typically, one of these ends would be held stationary and the loading press would exert pressure against the other one to move it toward the stationary end, thereby applying pressure to the respective end cap received in the cavity 84 of that end plate 78 or 80 and on to the sample specimen held within the sleeve 40 inside the body 24 of the triaxial load cell.

The embodiment of the specimen test device 22 shown in FIGS. 5 and 6 is the same as the embodiment shown in FIGS. 3 and 4 except that the end plates are larger and accommodate four connecting members instead of the two shown in the embodiment of FIGS. 3 and 4. This is indicated by the use of like reference numerals in FIGS. 5 and 6.

The aforementioned equipment can be used in performing the method of the present invention. This method is for testing the two-phase compressible composition, such as the foamed cementing composition. The composition can be made in a conventional manner which results in the composition having a gas under a pressure greater than atmospheric pressure. With regard to the system of FIGS. 1 and 2, the composition can be prepared in the vessel 2 which has the paddle 6. Relative rotation is created between the paddle 6 and the vessel 2 while a gas is flowed into the vessel under pressure greater than atmospheric pressure. This can initially be directly from the foaming fluid source 15 under its pressure. If this is the case, the pressure booster 16 is used later when the prepared composition is to be transferred to the specimen test device 22. Alternatively, the pressure booster 16 can be used during the initial creation of the composition in the vessel 2.

As an example of preparing a foamed cementing composition, one calculates the amount of unfoamed slurry and foaming materials (e.g., Halliburton foam additive and Halliburton foam stabilizer) to be placed into the vessel 2. These calculations are made using known equations for determining (1) specific gravity for the desired foamed slurry density, (2) the total amount of unfoamed slurry (including the foam additive and foam stabilizer) to be placed in the vessel 2, (3) the weight of the cement which is in the total weight of the slurry to be placed in the vessel 2, (4) the weight of the foam additive to be placed in the vessel 2 with the unfoamed cement slurry, (5) the weight of foam stabilizer additive to be placed in the vessel 2 with the unfoamed cement slurry, and (6) the weight of unfoamed base slurry (which has been prepared in an API mixer) to be placed into the vessel 2.

Preferably more cement (e.g., approximately twenty percent more) than is needed to be placed into the vessel 2 should be weighed and mixed to allow for slurry that will adhere to the mixing container in which the constituents are mixed before pouring into the vessel 2. A two quart Waring blender is a suitable mixing container for mixing slurries for use in the MACS Analyzer.

After mixing the slurry (without the foam additive and foam stabilizer), place the mixing container with the slurry on a balance, tare the balance (or measure the total weight of the slurry and mixing container), pour slurry into the MACS Analyzer vessel 2 until the desired test weight of the slurry (not including the foam additive and foam stabilizer) is in the chamber. This weight is determined by placing the mixing container with the remaining slurry back on the balance and obtaining a new weight (a negative weight on a digital balance indicates the grams placed into the chamber, or for a mechanical balance it is necessary to subtract the new weight from the original weight to determine the grams of slurry placed into the MACS Analyzer vessel 2).

Place the appropriate amount of foam additive and foam stabilizer into the vessel 2. A preferred procedure for obtaining the weight of foam additive and foam stabilizer in the vessel 2 is to fill a syringe with the foam additive (or foam stabilizer), empty the syringe, tare the syringe on a balance, refill the syringe with the proper amount of the foam additive (or foam stabilizer) and reweigh it on the balance to obtain the desired amount of each material, and transfer both materials into the MACS Analyzer vessel 2 containing the slurry.

Continuing with this non-limiting example, place the paddle into the vessel 2 and secure the lid. Install the drive belt from the magnetic drive, start the paddle rotating at 100 revolutions per minute (rpm), install and tighten a slurry thermocouple (or a plug), install and tighten the high pressure line and then increase the paddle speed to its maximum (approximately 1,000 rpm). With the PV pump valve and the Sprague pump valve of the MACS Analyzer closed, open the chamber isolation valve and screw in a nitrogen regulator connected to the foaming fluid source 15 to apply nitrogen pressure (e.g., 500 psi) to the vessel 2. Rotate the paddle at maximum speed (approximately 1,000 rpm) for five minutes after the pressure is applied. Reduce the paddle speed to 100 rpm for one minute, then reduce the speed to approximately two to three rpm which will be maintained during transferring of the slurry.

If the composition is made in the foregoing manner, the method of the present invention then includes increasing the pressure in the vessel 2 to a test pressure simulating a pressure in an oil or gas well. An example of this is a pressure up to about 11,000 psi (as opposed to the 500–1,500 psi from the foaming fluid source 15). The test pressure is greater than the pressure at which the composition is formed if the slurry is made in the foregoing manner using only the pressure available directly from the foaming fluid source 15. The increased pressure is obtained using the pressure booster 16 which boosts the pressure from the foaming fluid source 15. The pressure from the pressure booster 16 is communicated to the vessel 2 through the valve 68 and the inlet port 4 of the vessel 2.

In the method of the present invention, the specimen test device 22 is also pressurized. This includes pressurizing a first branch of the pressurizing system shown in FIG. 1 to the test pressure, pressurizing a second branch of the pressurizing system to the test pressure, and communicating the first branch with one portion of the specimen test device 22 and communicating the second branch with another portion of the specimen test device 22. The first branch of the pressurizing system includes the hydraulic fluid chamber 50, and the second branch of the pressurizing system includes the transfer flow collection chamber 52. Each of these is pressurized to the test pressure. The pressure from the hydraulic fluid chamber 50 is communicated to the exterior of the sleeve 40 in the triaxial load cell of the illustrated specimen test device 22, and the pressurized transfer flow collection chamber 52 is communicated with the interior side of the sleeve 40.

Using the system shown in FIGS. 1 and 2, the foregoing system pressurization of the method of the present invention is obtained by closing, or maintaining closed, valves 14, 54, 56, 12, 72, 74, 60 and 64 and opening valves 68 and 70. Valves 60 and 64 are then opened. This pressurizes the hydraulic fluid chamber 50 and the transfer flow collection chamber 52. The pressure shown by a gauge on a pressure regulator 96 and the pressure shown by a gauge on the pressure regulator 97 are compared to make sure the pressures are equal. If they are not, they are equalized using the valves of the respective regulators 96, 97. Once the pressures are equal, valves 54 and 56 are opened together (preferably simultaneously) to apply equal pressure to both sides of the sleeve 40 in the triaxial load cell of the specimen test device 22. Simultaneously applying equal pressures on both sides of the sleeve 40 prevents the sleeve 40 from being blown out or otherwise damaged by a significant pressure differential being applied across it. Gauges 92 and 93 are monitored to check for equal pressures. Valves 60 and 64 are left open during the foregoing.

When at least a portion of the composition in the vessel 2 is to be transferred to the specimen test device 22, this transfer occurs while maintaining a pressure at least substantially equal to the original test pressure on the transferred portion of the composition. Transferring the composition includes communicating the vessel 2 with the specimen test device 22 and relieving the pressure in the second branch of the pressurizing system containing the transfer flow collection chamber 52. The vessel 2 is communicated with the device 22 by opening (after first closing the valves 54 and 64) the valve 14 for the system shown in FIGS. 1 and 2. This communicates the pressurized vessel 2 with the pressurized interior of the sleeve 40 in the specimen test device 22. To relieve the pressure in the transfer flow collection chamber 52, pressure is bled off through the back pressure regulator 102. This can occur until a desired pressure differential exists across the specimen test device 22. In the FIG. 1 implementation, a differential pressure transducer 100 monitors the pressure across the specimen test device 22 through needle valves 105, 106 which are open until automatically closed in response to a predetermined pressure differential being sensed by the transducer 100.

The pressure differential allows flow from the vessel 2 into and through the specimen test device 22 and into and through the transfer flow collection chamber 52. Such a transfer of the composition from the vessel 2 is illustrated in FIG. 2 by the composition shown in the flow path between the vessel 2 and the ports of the chamber 52. Only a slight pressure drop (e.g., 1 or 2 psi) occurs between the vessel 2 and the valve 74. This slight pressure differential does not disrupt the pressurized state of the foamed cementing composition so that the gaseous phase of the composition is not lost. Because there is only the slight pressure differential between these portions of the fluid circuit, the pressure on the composition in the specimen test device 22 is at least substantially the initial test pressure (i.e., the nominal pressure would be somewhere between the level of the test pressure in the vessel 2 and the pressure in the transfer flow collection chamber 52). Although this also results in a slight pressure differential across the sleeve 40, the hardness or strength of the sleeve 40 is able to withstand this small pressure differential.

During the flow or transfer period, gauges 92–100 are monitored as are the lateral and longitudinal sensors of the triaxial load cell embodiment of the specimen test device 22. Valve 54 can be used to maintain pressure balance as required.

Once flow from the vessel 2 has started, the method further includes determining when a sufficient amount of the composition has been retained in the sleeve 40 of the specimen test device 22. This includes in the illustrated embodiment sensing a lateral dimension of the portion of the composition retained in the sleeve 40. This is determined by monitoring voltmeters connected to the lateral deflection sensors 75 illustrated in FIGS. 3–6. As the transferred composition builds up in the sleeve 40, the sensors 75 sense this and the connected voltmeters register readings. By appropriately calibrating these, one knows when the proper amount of the composition is retained in the sleeve 40. An initial indicator of composition flow is also obtained by observing a show of cement coming out of the valve 74 which can be used in the pressure relief action through chamber 52 as described above.

Because the composition also flows into and through the transfer flow collection chamber 52, the portion of the composition retained in the chamber 52 can be used for determining the density of the transferred composition. Thus, the method further comprises using the transfer flow collection chamber 52 containing this respective portion of the composition to test the density of the transferred composition. To determine density, the transfer flow collection chamber 52 is disconnected from the system and weighed. The empty chamber 52 is to have been weighed prior to installation and use in the system. Thus, the weight of the unloaded chamber 52 is subtracted from the weight of the chamber 52 loaded with the composition to determine the weight of the slurry in the chamber 52. Density is then determined using a known equation based on the two weights and the volume of the chamber 52. The chamber 52 is removed from the system only after closing the valves 56, 64 and 74 if it is to be disconnected with its internal pressure retained (which is preferred and which can include (1) using other valves not shown but connected to the ports of the chamber 52 and (2) connecting the valve 74 to the valve 56 after removal of the chamber 52). Once the chamber 52 has been used, it is discarded.

When it has been determined that a sufficient amount of the composition has been transferred into the sleeve 40 in the specimen test device 22, the valves 14 and 74 are closed while the valve 56 is left open. The valve 64 is opened during the curing process of the transferred material. Pressure is adjusted by monitoring the gauge 92 and adjusting via the valve 54 as required.

When the specimen is to be tested, the specimen test device 22 is disconnected from the vessel 2, the hydraulic fluid chamber 50, and the transfer flow collection chamber 52 while maintaining pressure in the specimen test device 22 such that the pressurized state of the portion of the composition in the specimen test device is not disrupted. This is done by closing (or maintaining closed) the valves 14, 54 and 56, which holds the pressure in the device 22. Valve 12 is then opened to dump the remaining composition out of the vessel 2 and to relieve the pressure in it, and valve 72 is likewise opened to dump the hydraulic fluid from the chamber 50 and relieve the pressure in it. The valve 74 is used to relieve the pressure from the line to the valve 56 (and from the chamber 52 if still attached). With the pressure in the respective vessels and chambers relieved, the lines leading into the valves 14, 54 and 56 opposite the specimen test device 22 are disconnected which removes the specimen test device 22 and these three valves from the system.

The foregoing assumes that the density tested through the chamber 52 is satisfactory. If not, the system needs to be cleaned and the entire procedure begun again with the preparation of a new composition. If the density is as desired, the portion of the composition transferred into the specimen test device 22 is tested while maintaining the pressure within the device 22.

To test the composition in the sleeve 40 of the specimen test device 22 disconnected along with the valves 14, 54, 56 from the rest of the system, the sample is cured for the desired length of time at a selected temperature (e.g., room temperature or heated with a heating jacket or temperature bath applied to the specimen test device 22) if this has not already been done. Once the composition has cured, the conventional tests performed with the specimen test device 22, such as the illustrated triaxial load cell, are performed in a conventional manner.

Such conventional testing includes loading the triaxial load cell such as with a compressive axial force applied to the end members 41, 42 so that the end members 41, 42 move relatively closer to each other and thereby exert a force on the sample held therebetween within the sealing member 40. Confining pressure is applied radially toward the sealing member 40 by the test pressure held by the closed valve 54. This simulates a well pressure and preferably can be up to at least about 11,000 psi. The core sample can also be heated by energizing the heating jackets. Heating preferably occurs until the temperature inside the sealing member 40 is at a temperature simulating a well temperature, such as up to 300° F.

With the desired conditions of the sample set, the resulting dimensional changes are sensed. This includes sensing the longitudinal or axial distance the sample is compressed as indicated by electrical signals provided by the linearly variable differential transducers of the longitudinal sensors in response to the movement between the two end members 41, 42. A measurement of the distance or length of deformation can be determined from the transducer signals as known in the art.

Sensing dimensional changes also includes sensing the radial distance the core sample is distended in response to the forces acting on the sample. The radial deformation is sensed by measuring at the four locations around the sample where the four linearly variable differential transducers 75 are located. Electrical signals from the transducers are used in known manner to provide measurements of the dimensional changes.

Because the dimensional changes represent axial and radial strain of the sample under the stresses applied by the exerted forces, the preferred embodiment further comprises determining Young's modulus and Poisson's ratio. This is done in known manner in response to the applied stress and resultant measured strain.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method for testing a two-phase compressible composition, comprising:

pressurizing the two-phase compressible composition in a first vessel to a pressure greater than atmospheric pressure, wherein the two-phase compressible composition is a cement slurry;

pressurizing a second vessel to the pressure;

transferring at least a portion of the cement slurry from the first vessel to the second vessel while maintaining at least substantially the pressure on the transferred portion of the cement slurry; and while maintaining at least substantially the pressure in the second vessel, allowing the cement slurry to harden and then testing the hardened cement in the second vessel.

2. A method as defined in claim 1, further comprising determining when a sufficient amount of the cement slurry has been transferred into the second vessel, including sensing a lateral dimension of the portion of the cement slurry retained in the second vessel.

3. A method as defined in claim 1, wherein the pressure simulates a pressure in an oil or gas well.

4. A method as defined in claim 3, wherein the two-phase compressible composition is a foamed cement slurry composition.

5. A method as defined in claim 1, wherein pressurizing a second vessel to the pressure includes:

pressurizing a first branch of a pressurizing system to the pressure;

pressurizing a second branch of the pressurizing system to the pressure; and communicating the first branch with a first side of a receptacle in the second vessel and communicating the second branch with a second side of the receptacle.

6. A method as defined in claim 5, wherein transferring at least a portion of the cement slurry includes communicating the first vessel with the second vessel subsequent to which there is cement slurry in the receptacle and relieving pressure in the second branch communicating with the second side of the receptacle while maintaining on the transferred cement slurry in the receptacle a pressure at least substantially equal to the pressure to which the second vessel was pressurized.

7. A method as defined in claim 6, further comprising, prior to testing the portion of the cement slurry transferred to the second vessel, disconnecting the second vessel from the first vessel and from the first and second branches of the pressurizing system while maintaining the pressure in the second vessel and on the receptacle therein.

8. A method as defined in claim 1, wherein the second vessel includes:

a triaxial load cell; and a support structure mounted on the triaxial load cell, the support structure including:

a first end plate, the first end plate disposed adjacent one end of the triaxial load cell;

a second end plate, the second end plate disposed adjacent another end of the triaxial load cell; and a plurality of connecting members slidably received by the first and second end plates, the connecting members defining a maximum spacing between the first and second end plates but permitting the first and second end plates to move relatively towards each other along the connecting members.

9. A method of testing a foamed cementing composition, comprising:

preparing a foamed cementing composition in a vessel having a paddle, including creating relative rotation between the paddle and the vessel and flowing a gas into the vessel under a pressure greater than atmospheric pressure;

increasing the pressure in the vessel to a test pressure simulating a pressure in an oil or gas well;

pressurizing a hydraulic fluid chamber to the test pressure;

pressurizing a transfer flow collection chamber to the test pressure;

communicating the pressurized hydraulic fluid chamber with the exterior of a sleeve retained in a specimen test device and communicating the pressurized transfer flow collection chamber with the interior of the sleeve in the specimen test device;

communicating the pressurized vessel with the interior of the sleeve in the specimen test device; and relieving the pressure in the transfer flow collection chamber to allow flow from the pressurized vessel to the pressurized transfer flow collection chamber such that a portion of the foamed cementing composition is transferred into the sleeve of the specimen test device without disrupting the pressurized state of the foamed cementing composition.

10. A method as defined in claim 9, further comprising:

determining when a sufficient amount of the foamed cementing composition is transferred into the sleeve in the specimen test device;

disconnecting the specimen test device from the vessel, the hydraulic fluid chamber and the transfer flow collection chamber while maintaining pressure in the specimen test device such that the pressurized state of the portion of the foamed cementing composition in the specimen test device is not materially disrupted; and testing the portion of the foamed cementing composition in the sleeve of the specimen test device under the maintained pressure.

11. A method as defined in claim 10, wherein determining when a sufficient amount of the foamed cementing composition is transferred into the sleeve in the specimen test device includes sensing through the sleeve lateral dimensions of the transferred portion of the foamed cementing composition.

12. A method as defined in claim 11, wherein increasing the pressure in the vessel to a test pressure includes boosting the pressure from a foaming fluid source used for preparing the foamed cementing composition and communicating the boosted pressure with the vessel.

13. A method as defined in claim 12, wherein another portion of the foamed cementing composition is transferred into the transfer flow collection chamber in response to relieving the pressure therein and wherein the method further comprises using the transfer flow collection chamber containing the respective portion of the foamed cementing composition to test the density of the transferred foamed cementing composition.

14. A method as defined in claim 9, wherein increasing the pressure in the vessel to a test pressure includes boosting the pressure from a foaming fluid source used for preparing the foamed cementing composition and communicating the boosted pressure with the vessel.

15. A method as defined in claim 9, wherein another portion of the foamed cementing composition is transferred into the transfer flow collection chamber in response to relieving the pressure therein and wherein the method further comprises using the transfer flow collection chamber containing the respective portion of the foamed cementing composition to test the density of the transferred foamed cementing composition.

16. A method as defined in claim 9, wherein the specimen test device includes:

a triaxial load cell having the sleeve therein; and a support structure mounted on the triaxial load cell, the support structure including:

a first end plate, the first end plate disposed adjacent one end of the triaxial load cell;

a second end plate, the second end plate disposed adjacent another end of the triaxial load cell; and a plurality of connecting members slidably received by the first and second end plates, the connecting members defining a maximum spacing between the first and second end plates but permitting the first and second end plates to move relatively towards each other along the connecting members.

17. A system for preparing, transferring and testing a foamed cementing composition, comprising:

a vessel to receive constituents for creating a foamed cementing composition under pressure;

a source of a fluid for foaming the cementing composition;

a pressure booster having an inlet connected to said source of a fluid and having an outlet connected to said vessel;

a specimen test device having a sleeve disposed therein;

a hydraulic fluid chamber;

a transfer flow collection chamber;

a first valve, said first valve connected to an outlet of said vessel and to an inlet of said specimen test device;

a second valve, said second valve connected to said hydraulic fluid chamber and to said specimen test device such that said second valve controls communication of pressure from said hydraulic fluid chamber with an exterior of said sleeve;

a third valve, said third valve connected to said transfer flow collection chamber and to said specimen test device such that said third valve controls communication of pressure from said transfer flow collection chamber with an interior of said sleeve;

means for connecting said pressure booster with said hydraulic fluid chamber; and means for connecting said pressure booster with said transfer flow collection chamber.

18. A system as defined in claim 17, wherein said specimen test device includes a triaxial load cell having said first, second and third valves connected thereto.

19. A system as defined in claim 15, wherein said specimen test device includes:

a triaxial load cell having said first, second and third valves connected thereto and having said sleeve therein; and a support structure mounted on said triaxial load cell, said support structure including:
  a first end plate, said first end plate disposed adjacent one end of said triaxial load cell;
  a second end plate, said second end plate disposed adjacent another end of said triaxial load cell; and
  a plurality of connecting members slidably received by said first and second end plates, said connecting members defining a maximum spacing between said first and second end plates but permitting said first and second end plates to move relatively towards each other along said connecting members.

20. A method for testing a two-phase compressible composition, comprising:
  pressurizing the two-phase compressible composition in a first vessel to a pressure greater than atmospheric pressure;
  pressurizing a second vessel to the pressure;
  transferring at least a portion of the composition from the first vessel to the second vessel while maintaining at least substantially the pressure on the transferred portion of the composition; and
  while maintaining at least substantially the pressure in the second vessel, testing the portion of the composition transferred to the second vessel;
  wherein pressurizing a second vessel to the pressure includes:
    pressurizing a first branch of a pressurizing system to the pressure;
    pressurizing a second branch of the pressurizing system to the pressure; and
    communicating the first branch with a first side of a receptacle in the second vessel and
    communicating the second branch with a second side of the receptacle.

21. A method as defined in claim 20, wherein the second vessel includes:
  a triaxial load cell; and
  a support structure mounted on the triaxial load cell, the support structure including:
    a first end plate, the first end plate disposed adjacent one end of the triaxial load cell;
    a second end plate, the second end plate disposed adjacent another end of the triaxial load cell; and
    a plurality of connecting members slidably received by the first and second end plates, the connecting members defining a maximum spacing between the first and second end plates but permitting the first and second end plates to move relatively towards each other along the connecting members.

22. A method as defined in claim 20, wherein transferring at least a portion of the composition includes communicating the first vessel with the second vessel subsequent to which there is composition in the receptacle and relieving pressure in the second branch communicating with the second side of the receptacle while maintaining on the composition in the receptacle a pressure at least substantially equal to the pressure to which the second vessel was pressurized.

23. A method as defined in claim 22, further comprising, prior to testing the portion of the composition transferred to the second vessel, disconnecting the second vessel from the first vessel and from the first and second branches of the pressurizing system while maintaining the pressure in the second vessel and on the receptacle therein.

* * * * *